United States Patent
Freeman

(10) Patent No.: US 6,587,713 B1
(45) Date of Patent: Jul. 1, 2003

(54) BRAINWAVE RESPONSIVE WHEELCHAIR

(76) Inventor: Bertha Freeman, 100-12 G Donizetti Pl., Bronx, NY (US) 10475

( * ) Notice: Subject to any disclaimer, the term of this patent is extended or adjusted under 35 U.S.C. 154(b) by 0 days.

(21) Appl. No.: 10/023,506

(22) Filed: Dec. 14, 2001

(51) Int. Cl.[7] ............................................. A61B 5/00
(52) U.S. Cl. ...................... 600/544; 600/586; 600/300
(58) Field of Search ............................ 600/554–5, 300, 600/586

(56) References Cited

U.S. PATENT DOCUMENTS

| | | | |
|---|---|---|---|
| 3,512,605 A | | 5/1970 | Mccorkle |
| 3,674,310 A | | 7/1972 | Montagano |
| 4,013,068 A | * | 3/1977 | Settle et al. ................ 600/544 |
| 4,075,438 A | | 2/1978 | Kappel |
| 4,767,940 A | * | 8/1988 | Tuttle ........................ 307/116 |
| 5,253,724 A | * | 10/1993 | Prior ........................... 180/65 |
| 5,301,975 A | | 4/1994 | Rivera |
| 5,363,858 A | * | 11/1994 | Farwell ..................... 600/544 |
| 5,692,517 A | * | 12/1997 | Junker ....................... 128/544 |
| D412,685 S | | 8/1999 | Bar et al. |
| 6,016,385 A | | 1/2000 | Yee et al. |
| 6,163,281 A | * | 12/2000 | Torch ......................... 341/21 |
| 6,349,231 B1 | * | 2/2002 | Musha ....................... 600/544 |

* cited by examiner

*Primary Examiner*—Robert L. Nasser

(57) ABSTRACT

A brainwave responsive wheelchair for providing control of an electric wheelchair by a physically handicapped person, includes a wheelchair having a seat portion, a back portion, a pair of back wheels and a pair of front wheels. A motor for selectively rotating the back wheels independent of each other is mechanically coupled to the back wheels. An actuator for selectively rotating the back wheels is operationally coupled to the motor. The actuator is mounted to the back portion and includes a control that is electrically coupled to the motor. A brainwave responsive device is operationally coupled to the control. The brainwave responsive device includes an input device. The input device is electrically coupled to the control and adapted for reading brainwaves. The control actuates the motor with respect to distinct brainwave patterns.

6 Claims, 2 Drawing Sheets

BRAINWAVE RESPONSIVE WHEELCHAIR

BACKGROUND OF THE INVENTION

1. Field of the Invention

The present invention relates to wheelchair devices and more particularly pertains to a new brainwave responsive wheelchair for providing control of an electric wheelchair by a physically handicapped person.

2. Description of the Prior Art

The use of brainwave actuated devices is known in the prior art. U.S. Pat. No. 4,949,726 describes a device for using brainwaves for controlling an apparatus. Another type of device is U.S. Pat. No. 6,097,981 which uses brainwaves for controlling animation.

While these devices fulfill their respective, particular objectives and requirements, the need remains for a device that incorporates brainwave actuated controllers and wheelchairs to provide mobility to handicapped persons who do not have viable motor skills or cannot communicate using conventional methods.

SUMMARY OF THE INVENTION

The present invention meets the needs presented above by coupling a brainwave reading device to the controls of an electric wheelchair such that the brainwave reading device ultimately replaces the conventional controls of an electric wheelchair.

Still yet another object of the present invention is to provide a new brainwave responsive wheelchair that also includes audible controls for an electric wheelchair.

To this end, the present invention generally comprises a wheelchair includes a seat portion, a back portion, a pair of back wheels and a pair of front wheels. A motor for selectively rotating the back wheels independent of each other is mechanically coupled to the back wheels. An actuator for selectively rotating the back wheels is operationally coupled to the motor. The actuator is mounted to the back portion and includes a control that is electrically coupled to the motor. A brainwave responsive device is operationally coupled to the control. The brainwave responsive device includes an input device. The input device is electrically coupled to the control and adapted for reading brainwaves. The control actuates the motor with respect to distinct brainwave patterns.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
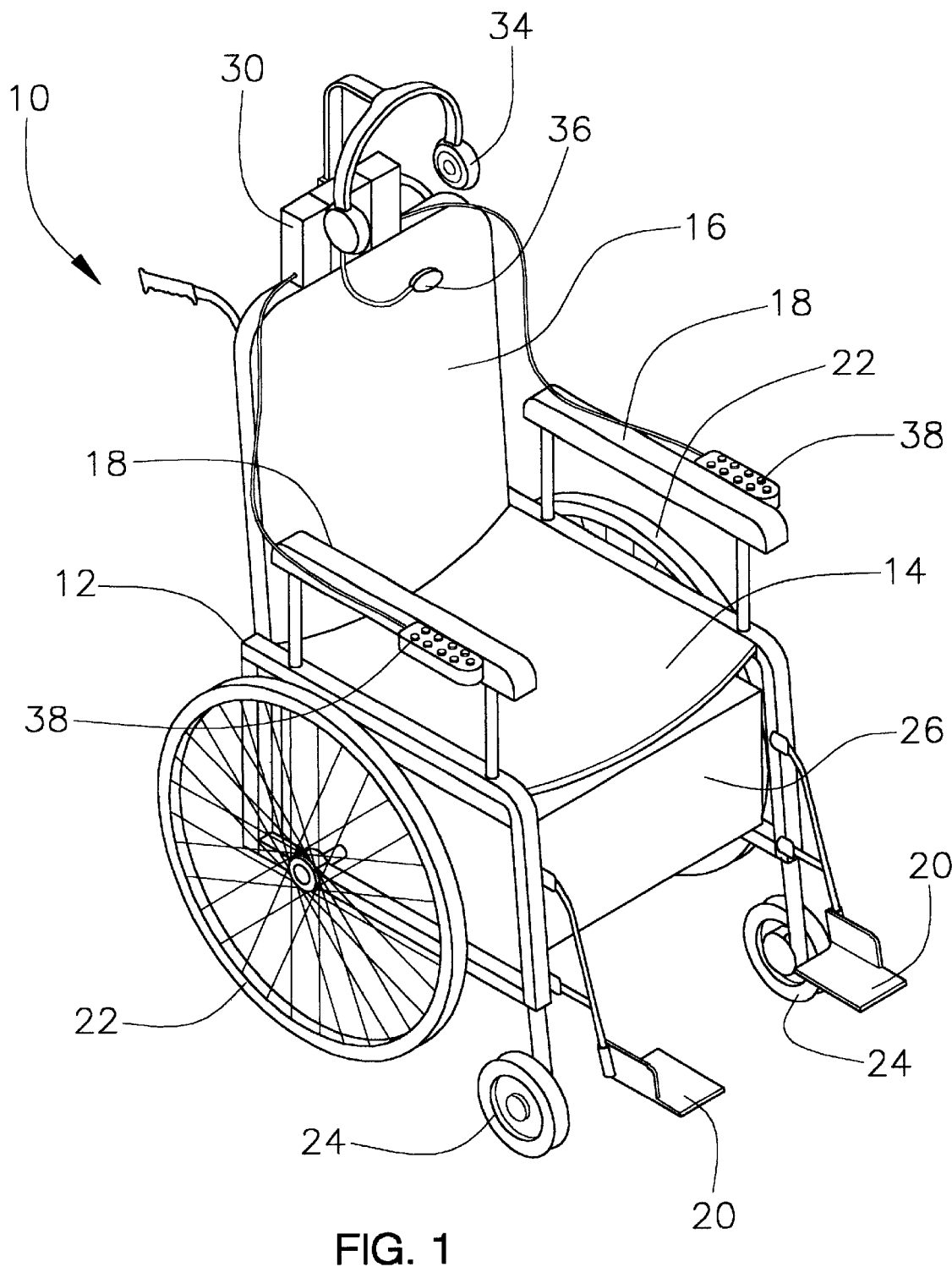
FIG. 1 is a schematic perspective view of a new brainwave responsive wheelchair according to the present invention.
Figure 2:
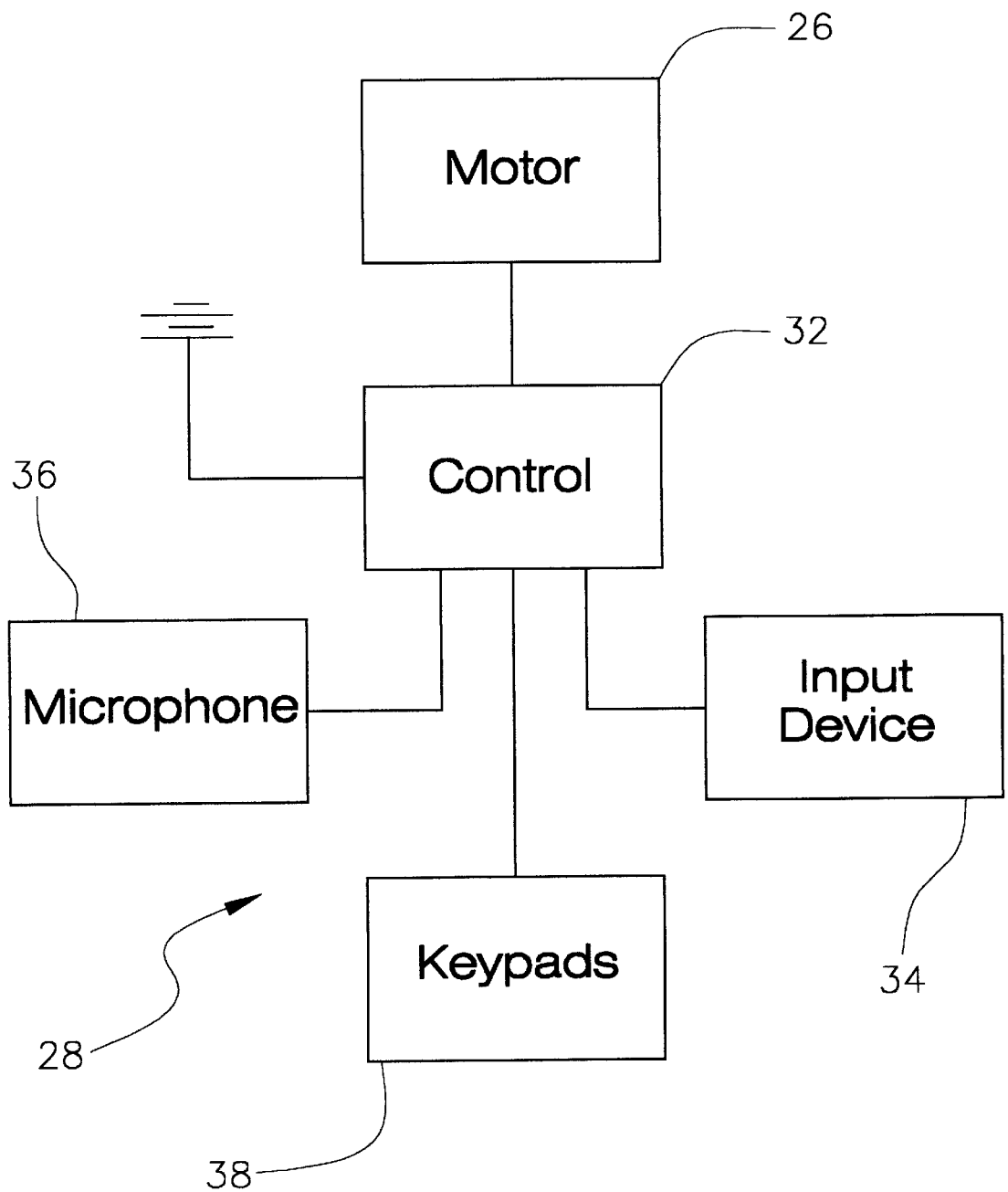
FIG. 2 is a schematic view of the present invention.

With reference now to the drawings, and in particular to FIGS. 1 and 2 thereof, a new brainwave responsive wheelchair embodying the principles and concepts of the present invention and generally designated by the reference numeral 10 will be described.

As best illustrated in FIGS. 1 and 2, the brainwave responsive wheelchair 10 generally comprises a wheelchair 12 including a seat portion 14, a back portion 16, a pair of armrests 18, a pair of footrests 20, a pair of back wheels 22 and a pair of front wheels 24. A motor 26 for selectively rotating the back wheels 22 independent of each other is mechanically coupled to the back wheels 22. The wheelchair 12 is generally a conventional electric wheelchair.

An actuator 28 for selectively rotating the back wheels 22 is operationally coupled to the motor 26. The actuator 28 includes a housing 30 mounted to the back portion 16. The actuator 28 includes a control 32 electrically coupled to the motor 15. The control 32 is mounted in the housing 30. The control includes a control processor.

A brainwave responsive device is operationally coupled to the control. The brainwave responsive device includes an input device 34 mounted on the housing 30 and located for being removably positioned on a head of a user of the wheelchair 12. The input device 34 is electrically coupled to the control 32 and adapted for reading brainwaves. The input device 34 includes an electroencephalograph. The control 32 actuates the motor 26 with respect to distinct, pre-programmed, brainwave patterns.

A microphone 36 for detecting audible tones is electrically coupled to the control 32. The microphone 36 is mounted on the housing 30 and is located to be positionable adjacent to a mouth of the user. The control 32 actuates the motor 26 with respect to specific spoken commands, pre-programmed in the control, detected by the microphone.

A pair of keypads 38 for actuating the motor 26 is operationally coupled to the control. Each of the keypads 38 is mounted on one of the armrests 18.

In use, a handicapped person may actuate the electric wheelchair in a number of ways. The user may use the keypad, spoken words, or brainwave patterns. When the control detects pre-programmed signals, from either the keypad, microphone or input device, the control sends the associated command to the motor for turning either one or both of the back wheels to provide the desired outcome.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A brainwave-responsive wheelchair comprising:

a wheelchair including a seat portion a back portion, a pair of back wheels and a pair of front wheels, a motor for selectively rotating said back wheels independent of each other being mechanically coupled to said back wheels;

an actuator for selectively rotating said back wheels being operationally coupled to said motor, said actuator being mounted to said back portion, said actuator including;

a control being electrically coupled to said motor;

a microphone for detecting audible tones being electrically coupled to said control, said microphone being located to be positionable adjacent to a mouth of the user, wherein said control actuates said motor with respect to specific spoken commands detected by said microphone; and a brainwave responsive device being operationally coupled to said control, said brainwave responsive device including an input device, said input device being electrically coupled to said control and adapted for reading brainwaves, wherein said control actuates said motor with respect to distinct brainwave patterns.

2. The brainwave-responsive wheelchair as in claim 1, wherein said input device is located for being removably positioned on a head of a user of said wheelchair.

3. The brainwave-responsive wheelchair as in claim 1, wherein said input device is an electroencephalograph.

4. The brainwave-responsive wheelchair as in claim 1, further including a keypad for actuating said motor being operationally coupled to said control, each of said keypads being mounted on one of said wheelchair.

5. The brainwave-responsive wheelchair as in claim 1, further including a keypad for actuating said motor being operationally coupled to said control, each of said keypads being mounted on one of said wheelchair.

6. A brainwave-responsive wheelchair comprising:

a wheelchair including a seat portion, a back portion, a pair of armrests, a pair of footrests, a pair of back wheels and a pair of front wheels, a motor for selectively rotating said back wheels independent of each other being mechanically coupled to said back wheels;

an actuator for selectively rotating said back wheels being operationally coupled to said motor, said actuator including a housing being mounted to said back portion, said actuator including;

a control being electrically coupled to said motor, said control being mounted in said housing;

a brainwave responsive device being operationally coupled to said control, said brainwave responsive device including an input device mounted on said housing and located for being removably positioned on a head of a user of said wheelchair, said input device being electrically coupled to said control and adapted for reading brainwaves, said input device including an electroencephalograph, wherein said control actuates said motor with respect to distinct brainwave patterns;

a microphone for detecting audible tones being electrically coupled to said control, said microphone being mounted on said housing and being located to be positionable adjacent to a mouth of the user, wherein said control actuates said motor with respect to specific spoken commands detected by said microphone; and a pair of keypads for actuating said motor being operationally coupled to said control, each of said keypads being mounted on one of said armrests.

* * * * *